United States Patent [19]

Mullis

[11] Patent Number: 5,187,083
[45] Date of Patent: Feb. 16, 1993

[54] RAPID PURIFICATION OF DNA

[75] Inventor: Kary B. Mullis, La Jolla, Calif.

[73] Assignee: Specialty Laboratories, Inc., Santa Monica, Calif.

[21] Appl. No.: 611,921

[22] Filed: Nov. 13, 1990

[51] Int. Cl.$^5$ .................... C12P 19/34; C12N 1/08; C12N 1/06

[52] U.S. Cl. .................... 435/91; 435/6; 435/259; 435/270; 435/803; 435/820; 536/23.1; 935/19; 935/20; 935/21

[58] Field of Search .................... 435/6, 91, 270, 259, 435/820, 803; 536/27; 935/19–21

[56] References Cited

U.S. PATENT DOCUMENTS 4,900,677  2/1990  Hewitt .................... 435/270
4,997,932  3/1991  Reardon et al. .................... 435/6
5,063,162  11/1991  Kiefer .................... 536/27

Primary Examiner—Herbert J. Lilling
Attorney, Agent, or Firm—Poms, Smith, Lande & Rose

[57] ABSTRACT

The present invention provides a method for rapidly obtaining substantially pure DNA from a biological sample containing cells. The method involves gently lysing the membranes of the cells to yield a lysate containing genomic DNA in a high molecular weight form. The lysate is moved through a porous filter to selectively trap the high molecular weight DNA on the filter. The DNA is released from the filter using an aqueous solution to form a solution containing substantially purified DNA, from which the DNA is recovered.

29 Claims, 3 Drawing Sheets

RAPID PURIFICATION OF DNA

The research reported in this application in support of the invention herein received assistance from a grant provided by the Department of Health & Human Services, Public Health Service, Grant No. 1R01HL43532-02.

The present invention relates to a method for rapidly purifying DNA from cells and tissues and more particularly to a method for rapidly obtaining substantially purified DNA from whole blood.

BACKGROUND OF THE INVENTION

In recent years, the contamination of the human blood supply with a variety of life-threatening and debilitating viruses, such as retroviruses, including HIV (AIDS) has generated a need for a rapid, inexpensive method to purify DNA from human tissues so as to detect viral DNA in human blood. Tests to detect viruses in blood traditionally detect antibodies specific for such viruses. If the nucleic acid sequence of a pathogenic virus is known, the presence of that virus in cells and tissues can be detected in DNA purified from the biological sample. However, it is easier to rely on serological tests of the virus' presence than a test for detecting the viral-specific DNA. Serological tests detect a subject's antibody production against the viral agent. Tests for detecting the presence of antibodies are more efficient and easier to perform than tests for detecting the presence of viral DNA in tissues. Purification of cellular DNA to detect the presence of viral-specific DNA incorporated into genomic DNA requires hours of complicated cell/tissue lysate preparation and treatment.

These tests, however, fail to detect the presence of the virus early in the infection, before an individual mounts a detectable antibody response to the viral agent. Tests to directly detect viruses are also available but they are not practical, not easy to perform, and they are expensive. They include virus culture. Virus culture is not practical for mass screening of blood because up to a month is required to complete the culture. Alternatively, upon purification of DNA from tissues and cells, conventional nucleic acid hybridization techniques for the detection of viral nucleic acid (Ausubel, F. M., et al. eds., *Current Protocols in Molecular Biology*, John Wiley & Sons (1987)) could be carried out. Although the sensitivity of such hybridization techniques may be enhanced by amplifying the amount of viral DNA with the polymerase chain reaction (PCR), (Mullis, K. et al. *Methods in Enzymology*, 155:335 (1987)) which amplifies DNA in a sequence-specific manner, nonetheless, the DNA, if it is desired to use a large starting amount, must be first purified substantially free of proteins and RNA. Current methods for purifying DNA are too costly for use in mass screening. For mass screening purposes which involve testing of substantially large amounts of purified DNA for the presence of viral specific DNA sequences, a less involved method for sample preparation would be desirable. Clearly, a method for detecting the presence of viral DNA in the absence of detectable antibody is important to ensure that a blood supply is free from virus contamination.

Purifying DNA from tissue or cell samples is complicated, time consuming, and requires chemicals and equipment that are hazardous and/or expensive. Most current methods for DNA preparation use traditional organic solvent extractions and/or absorption columns. In general, optimal recovery of DNA from biological samples is achieved by a phenol extraction followed by ethanol precipitation. This requires training and technical skills so that DNA is obtained substantially free of proteins and RNA.

Clinically useful applications of DNA purification from human tissues, for example, involve the detection of disease-causing, viral-specific genomes incorporated into human chromosomes, such as human immunodeficiency virus (HIV). Another useful application is the detection of disease causing genes, such as cystic fibrosis, sickle cell anemia, and Duchenne muscular dystrophy.

Kits are now available which allow DNA isolation from tissues without the use of phenol/chloroform extraction. For example, A.S.A.P.™ Genomic DNA Isolation Kit, Boehringer Mannheim Biochemicals, Indianapolis, Ind.; and The Extractor™, Molecular Biosystems, Inc., San Diego, Calif. These kits employ an ion exchange column to retain DNA on the basis of DNA's electrical charge. A disadvantage of these kits is that the entire procedure from cell lysis to elution of purified DNA requires two to four hours for most samples.

Known procedures for DNA purification from whole blood require cumbersome and time consuming steps for cell lysate preparation. The multitude of steps creates a greater potential for specimen confusion and cross contamination. For example, to obtain purified cellular DNA, including viral-specific DNA, from a sample of whole blood, the red blood cells must first be separated from the nucleated white blood cells which contain the DNA. A typical method for preparing specimens of whole blood to purify DNA involves first purifying the mononuclear cells by banding in a density gradient such as ficoll hypaque (Pharmacia, Inc.) washing, then lysing the cells. The cell purification step is necessary because hemoglobin is reported to interfere with the PCR amplification. The isolated mononuclear cells are washed twice with phosphate buffered saline (PBS), then resuspended in 1 ml of PBS. A smear of the cell suspension is made and stained with Wright stain. The proportion of mononuclear cells is consistently found to be greater than 95%. A white cell count is then determined in a Coulter counter on an aliquot of each cell suspension. The cells are then pelleted and lysed by a quick lysis method to give a minimum cell concentration of $3 \times 10^6$ cells per ml. Proteinase K is added to a final concentration of 120 micrograms/ml and the lysates are incubated at 60° C. for 1 hour. The proteinase K is then inactivated by a 10-minute incubation at 95° C.

Mass screening of the human blood supply would require a mass scale-up of a traditional DNA purification method to detect viral-specific DNA. The cost would be very high for scaling up these methods to purify DNA obtained from either large numbers of samples or large sample volumes collected from a large portion of the population. Accordingly, it is desirable to have a method for rapidly, simply, and inexpensively obtaining purified DNA from small or large volumes or numbers of samples of donated human blood or other tissues.

Furthermore, it would be beneficial if such a simple procedure suitable for rapidly purifying DNA yielded the DNA substantially free of contaminants that can interfere with hybridization techniques or the polymerase chain reaction. Such contaminants include RNA, heparin, detergents, and large amounts of some proteins, like hemoglobin. It would be further desirable for this simple method to yield large amounts of DNA that can be examined for the presence of a single copy of a targeted sequence using the PCR.

Therefore, there is a need for a convenient and reliable technique for purifying large amounts of DNA from biological tissue or cell samples that requires less time than current techniques and does not require organic, hazardous, or expensive reagents. A technique is also needed which can be inexpensively and easily scaled up or down, does not require prior separation of cells from the sample, such as red blood cells, and that yields purified DNA that is substantially free of RNA, proteins, and other contaminants interfering with detection of specific DNA sequences by hybridization and amplification techniques, including polymerase chain reaction techniques.

SUMMARY

A method for obtaining substantially purified DNA from biological samples embodying features of the present invention satisfies these needs. The method provides for rapidly obtaining substantially pure DNA from a biological sample containing cells. While a preferred biological sample is whole blood, the method can be used for a variety of samples containing cells and tissues from mammalian, bacterial, yeast and plant sources.

The method comprises a first step of gently lysing the membranes of the cells in the biological sample. Gentle lysing releases the contents of the cells as a lysate containing DNA in a high molecular weight form. The lysate is then moved through a porous filter to selectively trap the high molecular weight DNA on the filter. The DNA trapped on the filter is high molecular weight DNA comprising more than about 500,000 base pairs. After trapping the high molecular weight DNA on the filter the method of the present invention provides for releasing the DNA from the filter using an aqueous solution to form a solution containing the DNA. The DNA released from the filter is recovered in substantially purified form from the solution.

The filter includes a surface that reversibly and specifically initially retains the high molecular weight DNA. The surface of the filter can be a porous substrate, which can typically be selected from at least one of the group of materials consisting of cellulose acetate, nitrocellulose, polyvinylidene and polycarbonate. The substrate can be a membrane filter. The pore size of the substrate can be from about 0.2 microns to about 0.8 microns. A preferred filter comprises a membrane filter comprised of cellulose acetate and nitrocellulose having a pore size of about 0.45 microns.

The step of gentle lysing involves contacting the cells in the biological sample with a detergent, typically sodium dodecyl sulfate, in sufficient concentration to rupture the membranes, including nuclear membranes, and release the contents of the cells as a lysate containing high molecular weight DNA. The invention provides for rendering the membranes of the cells more susceptible to detergent lysis of their membranes. Such rendering includes treatment of the biological sample with a proteinase.

After the step of gently lysing the cells, the present invention provides for the step of moving the lysate through the filter so that the filter selectively traps the high molecular weight DNA contained in the lysate. Movement of the lysate through the filter can be facilitated by suction filtration or by centrifugation.

The present invention provides for releasing the trapped DNA from the filter using an aqueous solution to form a solution containing the DNA. The DNA is released from the filter in a substantially purified form. The present invention contemplates releasing the DNA trapped on the filter by contacting the DNA with a sufficient amount of an aqueous solution containing divalent cations or restriction enzyme. A preferable aqueous solution for releasing the DNA from the filter contains 10 mM magnesium.

BRIEF DESCRIPTION OF DRAWINGS

Filter 2 is a similar photograph illustrating the DNA content of a lysate of whole human blood before and after filtration.

DETAILED DESCRIPTION

In order that the invention herein described may be more fully understood, the following detailed description is set forth.

According to the present invention, a method is provided for rapidly obtaining substantially pure DNA from a biological sample in less than about 30 minutes. The method comprises the steps of (a) gently lysing the membranes of the cells in a biological sample to release the contents of the cells as a lysate containing DNA in high molecular weight form for trapping on a filter; (b) moving the lysate through a porous filter to selectively trap the high molecular weight DNA on the filter; (c) releasing the high molecular weight DNA from the filter using an aqueous solution to form a solution containing the DNA; and (d) recovering the DNA in substantially purified form from the solution. The invention contemplates that such high molecular weight DNA comprises DNA having more than about 500,000 nucleotide base pairs.

The method of the present invention comprises a first step of gently lysing the membranes of the cells in a biological sample to release the contents of the cells as a lysate containing DNA in high molecular weight form. Lysis herein is the physical disruption of the membranes of the cells, referring to the outer cell membrane and, when present, the nuclear membrane.

The invention contemplates the use of a chemical detergent agent, preferably sodium dodecyl sulfate, for gently lysing the membranes of the cells. The invention contemplates other detergent chemical agents for lysing the membranes of the cells, including but not restricted to Triton-X100 TM and, NP-40 TM. The method of the invention concerns gently lysing the membranes of the cells in a biological sample by chemical means along with gentle swirling of the vessel in which lysis is carried out. Gentle lysis is defined herein as the avoidance of strong shear forces, such as those created by excessive pipetting, vortexing, or sonicating a solution containing DNA, such that DNA in the cells is converted to low molecular weight fragments. Gentle lysis in the method of the present invention provides shear forces sufficiently mild to yield a cell lysate with the majority of the genomic DNA in the form of high molecular weight having more than about 500,000 nucleotide base pairs per fragment. The present method separates the high molecular weight DNA from other components in the lysate by moving the lysate through a porous filter on which the high molecular weight DNA is trapped. The invention embodies lysing that is sufficiently gentle so as to produce a lysate containing DNA containing high molecular weight DNA, i.e. greater than approximately 500,000 nucleotide base pairs, that is selectively trapped on a porous filter when the lysate is moved through the filter.

Biological samples contemplated by the method of the present invention can be derived from mammalian, plant, bacterial and yeast sources. The biological sample can be in the form of single cells or in the form of a tissue. Cells or tissue can be derived from in-vitro culture. Where the cells of the biological sample are less susceptible to gentle lysis, the method of the present invention contemplates rendering the cells more susceptible to detergent lysis. Rendering can be achieved by treating the biological sample with a proteolytic agent such as proteinase K as the cells are contacted with detergent (Ausubel, F. M., et al. eds., Current Protocols in Molecular Biology, p. 2.2.2, John Wiley & Sons (1987)). Cell which are less susceptible to detergent lysis include those with cell walls, that is, bacteria, yeast, and plant cells. Cells embedded in tissues can be also be made more susceptible to gentle lysis by treating the tissue with proteinase K. ibid.

After gently lysing the membranes of the cells to release the contents of the cells as a lysate containing DNA in high molecular weight form, the invention provides for the step of moving the lysate through a porous filter to selectively trap the high molecular weight DNA on the filter.

The filter provided by the present invention incorporates a surface that selectively and reversibly traps substantially all of the high molecular weight DNA in the lysate. The surface of the filter can be a porous substrate comprised of a material selected from at least one of the group consisting of cellulose acetate, nitrocellulose, polyvinylidene, or polycarbonate. The porous substrate is preferably cellulose acetate and more preferably a mixture of cellulose acetate and nitrocellulose. A prefered form of the porous substrate is a membrane filter having a pore size from about 0.2 microns to about 0.8 microns. A most preferable filter is a membrane filter comprised of cellulose acetate and cellulose acetate having a pore size of about 0.45 microns.

According to the present invention, the lysate is moved through the filter at a rate of about 0.025 ml/cm$^2$/minute to about 0.5 ml/cm$^2$/minute. The rate is preferably about 0.25 ml/cm$^2$/minute. The invention contemplates moving the lysate through the filter by suction filtration (see Examples 3-7) or by centrifugation (see Examples 1 and 2), but the invention is not limited to these two methods for moving the lysate through the filter.

Whole blood is a typical biological sample containing cells whose outer and nuclear are gently lysed by the method of the present invention. The red blood cells in human blood are not nucleated and do not contain genomic DNA, but the white cells do contain nuclei with genomic DNA. In a typical protocol contemplated by the present invention, as described below in Example 3, whole blood was gently lysed by mixing, along with gentle swirling, a 100 microliter aliquot of whole blood with lysis buffer and incubating for 5-10 minutes. The filtrate of whole blood lysate contained substantially all of the hemoglobin and substantially all of the other cellular and noncellular proteins of the blood. All of the components of the lysate, with the exception of the high molecular weight DNA, were apparently not trapped by the filter device and moved through the filter into the filtrate. If components of the lysate (other than the high molecular weight DNA) were trapped by the filter, it was apparent that they were not released by the method provided by the invention for releasing the DNA from the filter. Furthermore, the eluate from the filter after release of the DNA was in a substantially purified form of DNA as indicated by O.D. 260/280. The purity of DNA obtained by this method can be established by the ratio of absorbance at 260 nm to the absorbance at 280 nm. For highly purified DNA, this ratio is about 1.8 (Ausubel, F. M., et al., eds., Current Protocols in Molecular Biology, p. 2.2.3, John Wiley & Sons, New York, 1987).

Athough not wishing to be bound by the following theory, it is believed that high molecular weight DNA released by gentle lysis of cells is trapped on the porous filter by virtue of the fact that the DNA chains are considerably longer than the inter-pore distance on the surface of the filter such that separate regions of a single high molecular weight DNA chain may be simultaneously drawn into different pores, thus preventing complete passage of the molecule through either pore. Accordingly, the high molecular weight DNA molecule is effectively trapped on and/or in the filter.

The present invention embodies the step of releasing the trapped DNA from the filter using an aqueous solution to form a solution containing the DNA. The high molecular weight DNA trapped on the filter can be released by contacting the filter an eluent comprising substantially pure water (see Example 6).

A preferred aqueous solution for releasing the high molecular weight DNA from the filter to form a solution containing DNA comprises a sufficient concentration of divalent cations, having a concentration from about 1 mM to about 100 mM. The invention more preferably employs a solution comprising 10 mM magnesium for releasing the high molecular weight DNA. The method also contemplates heating the filter device containing the trapped DNA in the presence of an aqueous solution. As shown in Example 7, DNA release is more efficient at 60° than at room temperature. A most preferred method contemplated by the present invention for releasing the high molecular weight DNA trapped on the filter employs contacting the filter with microwave radiation in the presence of a 10 mM magnesium solution to form a solution containing substantially purified DNA, as illustrated in Example 7 below.

Although not restricted to the following explanation, it is conjectured that high molecular weight DNA trapped in a porous membrane filter by the method of the present invention can also be released by cleaving the DNA into shorter, less easily trapped fragments. Cleavage achieves release of the DNA from the filter device by converting the long chains of DNA into shorter pieces that either diffuse off the top of the filter into eluant buffer or can be drawn with eluant buffer through the porous filter into the eluate. Although not wishing to be bound by any theory, the restriction enymatic release of the high molecular weight DNA trapped in the filter (see Example 7) is consistent with the hypothesis that the high molecular weight DNA is trapped physically on the filter. The trapped DNA extends outside of the filter. Breaking of bonds holding the DNA to the filter can be accomplished by DNA cleavage alone.

According to the present invention, a step is provided for recovering DNA in a substantially purified form. The invention contemplates recovery methods that involve removal of either all of the eluate or aliquots of the eluate solution containing substantially purified DNA released from the filter device. Such aliquots, as illustrated in the Examples below, can be subjected to a variety of analytical and synthetic techniques, such as described in Ausubel, supra or in *Molecular Cloning: A Laboratory Manual,* Cold Spring Harbor, (1982).

Examples of devices for using the method of the present invention include standard laboratory filter holders and filters furnished by companies such as Millipore, Inc., Biorad, Inc., MSI, inc., and Whatman, Inc. The method of the invention can be conducted in filtration devices which faciliate the movement of solutions through filters by means including centrifugation, suction, pressure.

In order that the invention described herein may be more fully understood, the following examples are set forth. It should be understood that these examples are for illustrative purposes only and are not to be construed as limiting the scope of this invention in any manner.

EXAMPLE 1

Capture and Elution of DNA From Whole Blood on Centrifuge Filters—Effect of Magnesium

Capture

Whole blood samples from human volunteers were collected into heparinized or EDTA containing tubes. 100-microliter aliquots were transferred to 1.7 ml Eppendorf tubes. 900 microliters of lysis buffer, SDS/1X in Dulbecco phosphate buffered saline (SDS/PBS) consisting of 138 mM NaCl, 8.1 mM $Na_2HPO_4$, 0.5 mM $MgCl_2$, 1.1 mM $KH_2PO_4$, and 2.7 mM KCl were added with gentle swirling. The resulting lysate was allowed to stand at room temperature for 5–10 minutes, after which 750 microliters of each were moved or passed through a Costar Spin-X ™ (Cambridge, Mass.) centrifuge filter unit having a 0.22 micron cellulose acetate membrane filter. This filter served to selectively trap the high molecular weight DNA and separate it from the lysate. Each filter was then washed twice with 750 microliters of an SDS/PBS solution. This was followed by two passes of 750 microliters of 50 mM Tris chloride at pH 7.4.

Elution 100 microliters of 50 mM Tris chloride, pH 7.4, containing 10 mM $MgCl_2$ was then pipetted into each filter contained in a Costar filter unit and the units were gently rocked at 37° C. for 10 minutes. The tubes were centrifuged and the filtrate recovered for gel analysis of the DNA. A further aliquot of the elution buffer was added to the filters and after 20 minutes at room temperature the elution buffer was filtered through and analyzed.

Results

Figure 1:
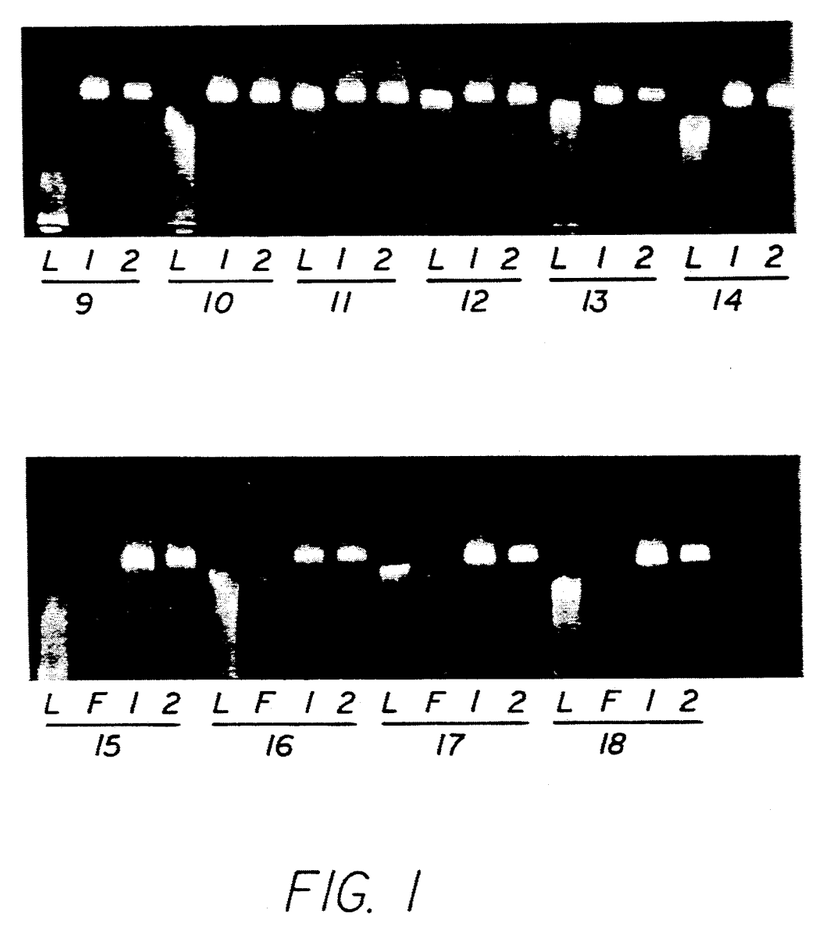
FIG. 1 is a photograph of an agarose gel illustrating the distribution of DNA in a lysate of human whole blood, the filtrate of the lysate, and eluates of the filter.

The DNA was quantitatively released by the lysis procedure and efficiently trapped on the filters as indicated by agarose gel electrophoresis (see FIG. 1). The top row of FIG. 1 shows that the DNA was released in solution and recovered in that solution from the filters by elution with a buffer containing magnesium. The lanes labeled "L" each contained an aliquot of lysate before the lysate was moved through the filter. The lanes labeled "1" each contained an aliquot of magnesium-containing elution buffer which was run through the filter through which the lysate was previously moved. The lanes labeled "2" each contained an aliquot of magnesium-containing buffer run through the filter subsequent to the previous run-through of magnesium-containing buffer.

The bottom row of the gel shows the removal of the DNA from the lysate by the filter as a result of moving the lysate through the filter. The bottom row further shows that the DNA selectively trapped on the filter was subsequently removed by passing magnesium-containing elution buffer through the filter containing the trapped DNA. The lanes labeled "L," contained an aliquot of lysate, the lanes labeled "F" contained an aliquot of the filtrate of the lysate moved through the filter; and the lanes labeled "1," and "2" contained aliquots of magnesium-containing buffer, as above.

Approximately 10% of the DNA trapped on the filter was released and recovered.

EXAMPLE 2

Distribution of DNA in Lysate Before and After Lysate Moved Through Filter and Treated with Various Washes The purpose of this example was to show the removal of high molecular weight DNA from the lysate by the filter. As in Example 1, above, heparinized, human whole blood was collected, gently lysed, and transferred to a centrifuge filter unit. The centrifuge filter unit served as the filter for retaining the high molecular weight DNA. The centrifuge unit was spun for three minutes in a bench top centrifuge so as to move the lysate through the filter device by centrifugation. The filter was then washed sequentially with 750 microliter of (a) lysis buffer, (b) 50 mM Tris hydrochloride at pH 7.4, (c) (b) plus 10 mM magnesium chloride, and (d) a second aliquot of (c).

10 microliter aliquots of each fraction were applied to an agarose gel and electrophoresed at 20 volts/cm for thirty minutes. DNA was detected with ethidium bromide staining and ultraviolet light as described by Ausubel, F. M., et al., eds. *Current Protocols in Molecular Biology,* p. 2.5.4, John Wiley & Sons, New York, 1987. The fractions applied were as follows:

1. whole lysate
2. filtered lysate
3. lysis buffer wash
4. 50 mM Tris wash
5. first magnesium elution
6. second magnesium elution
7. 1/20th of (5)
8. repeat of (5)

Figure 2:
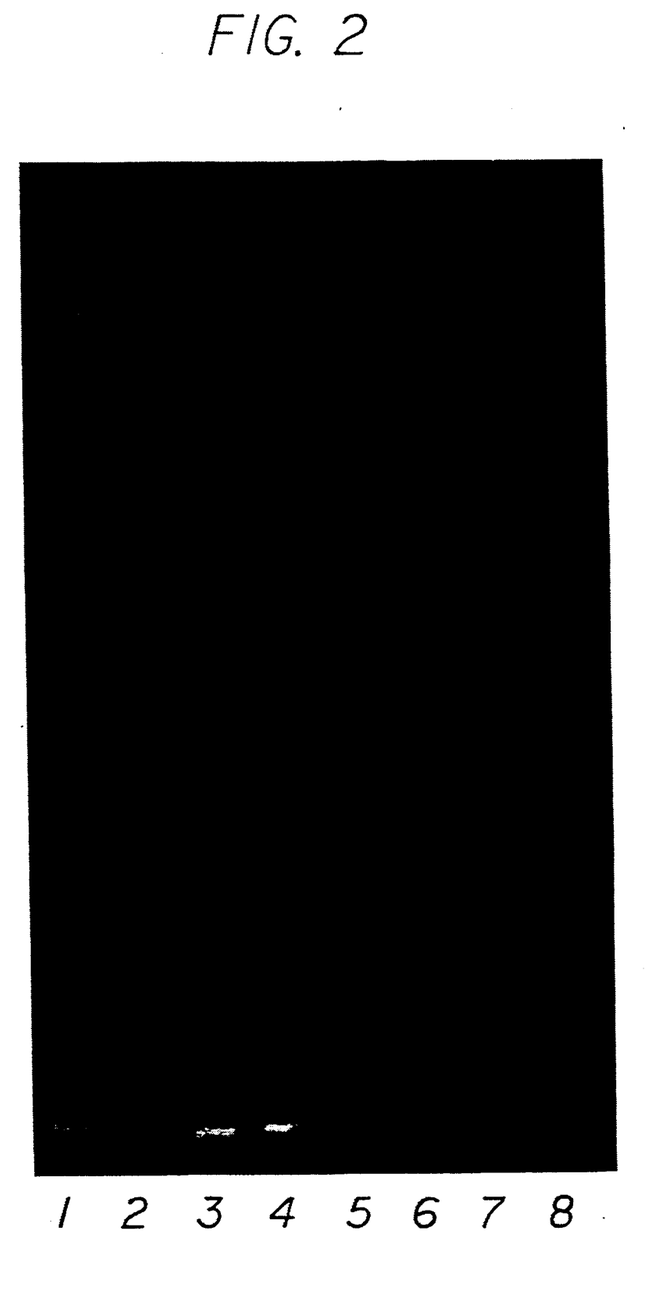

FIG. 2 depicts the results of agarose gel electrophoresis of these samples. Lane 1 contained a 10 microliter aliquot of the whole lysate, the total volume of which was 1 milliter. Lane 2 contained a 10 microliter aliquot of the whole lysate following movement through the filter device. Lane 3 contained a 10 microliter aliquot of the lysis buffer wash. Lane 4 had a 10 microliter aliquot of the Tris buffer wash. Lane 5 contained a 10 microliter aliquot of the first elution with the buffer containing magnesium. Lane 6 contained a 10 microliter aliquot of the second elution with the buffer containing magnesium. Lane 7 contained 0.5 microliters of the first elution containing magnesium buffer. Lane 8 is a duplicate of lane 5.

Approximately 5% of the DNA present in the whole lysate was recovered after the first magnesium elution. After the second magnesium elution, an additional 5% of the DNA in the whole lysate was recovered.

EXAMPLE 3

Trapping and Elution of DNA from Whole Blood in a Millipore ™ Filtration Apparatus The purpose of this example was to explore the convenience and effectiveness of larger diameter filters for rapidly purifying DNA using the method of the present invention. Ten ml of human whole blood was drawn into a heparainized tube. The blood was gently lysed by the addition and admixture by gentle swirling at room temperature of 90 ml of lysis buffer, 1% SDS in 1X Dulbecco phosphate buffered saline consisting of 138 mM NaCl, 8.1 mM $Na_2HPO_4$, 0.5 mM $MgCl_2$, 1.1 mM $KH_2PO_4$, and 2.7 mM KCl. At 5-10 minutes post lysis, a 5 ml aliquot of the lysed blood volume was vacumn-filtered through a 0.45 micron cellulose acetate membrane filter, 2.5 cm diameter, MSI, Inc. (Westboro, Mass.). The membrane was then washed twice with 3 to 5 ml of the lysis buffer and then 3 to 5 ml of the wash buffer, 50 mM Tris-HCl, pH 7.4. These washing steps were done with squeeze bottles containing the aforementioned solutions and were not carefully controlled with respect to volume. However, care was taken to completely wash the filter device until the filter was colorless. Completeness in the Tris buffer wash, which was used to remove SDS, was judged by the absence of foaming in the filter well on application of the final aliquot of wash buffer. Two 3-5 ml washes were adequate to accomplish these ends.

The filters were removed from the vacumn manifold and placed into 1 ml aliquots of an elution buffer containing 80 mM Tris-HCl at pH 9.0, 20 mM ammonium sulfate, 10 mM magnesium chloride in the shallow well of CoStar ™ (Cambridge, Mass.) plastic cell culture dishes. The dishes were placed in a rotary shaker for several hours at 37° C., at which time they were discovered to have evaporated to dryness. After addition of 1 ml aliquots of water, the dishes were placed back into the shaker for 30 minutes and aliquots taken for analysis.

Results and Conclusions

Filtration times for movement of the lysate through the filter, were less than one minute. DNA recovered from cellulose acetate under all conditions was 100% as judged from agarose gel electrophoresis as shown FIG. 3.

Figure 3:
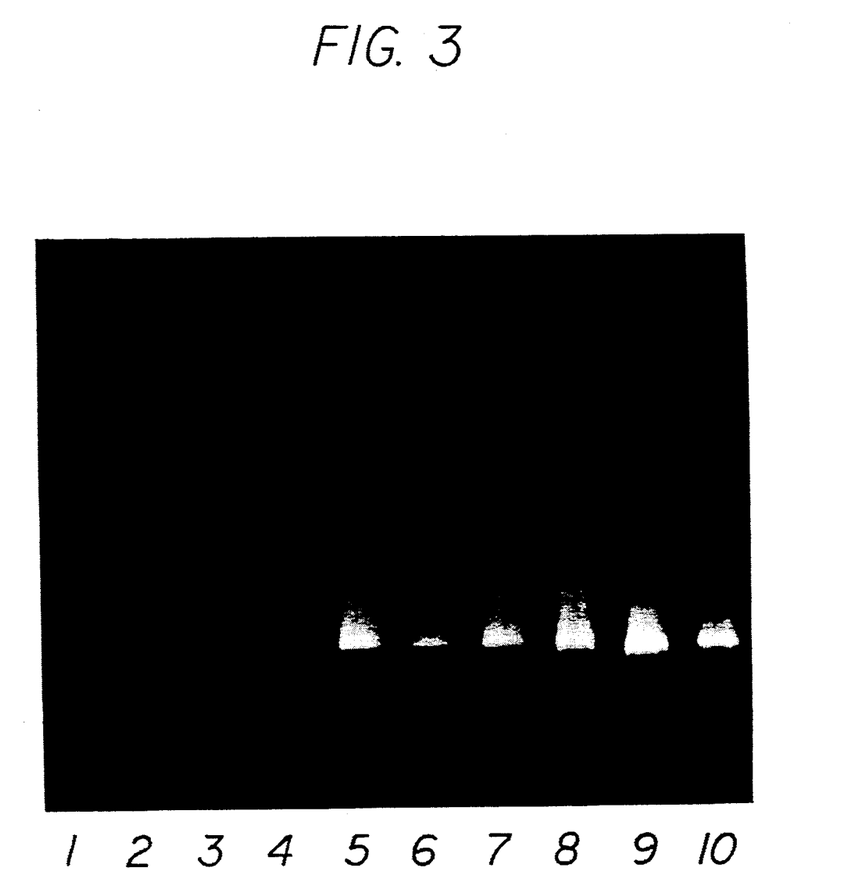
FIG. 3 is similar photograph illustrating a comparison of DNA contained in lysates, filtrates, and eluates of whole human blood to standard amounts of human genomic DNA.

Lanes 1 and 2 contained aliquots of human DNA standards, each containing the equivalent of 10,000 copies of the human genome. These lanes served as a direct comparison to lanes 3 and 4, indicating that the release of DNA from the cells by the lysis buffer was complete. It should be noted in lanes 3 and 4 that the lysis buffer containing SDS interfered with the mobility of the DNA on the agarose gel. Lanes 5-10 consisted of aliquots containing DNA released from the filter device by the elution buffer. 100% efficency for the entire process would be indicated by DNA bands that were five times brighter than the standards in lanes 1 and 2. The brightness of lanes 5-10 indicated DNA recoveries in the 50% to 100% range, recoveries considerably higher than the approximately 10% recoveries observed in FIGS. 1 or 2 (Examples 1 and 2) above.

EXAMPLE 4

Comparison of Nitrocellulose and Cellulose Acetate Filters

The purpose of this experiment was to compare the abilities of nitrocelluose and celluose acetate filters to specifically and reversibly retain DNA released from recently lysed cells; and to determine if time elapsed between lysis and movement of lysate through a filter had a significant effect on filtration time or DNA recovery.

Ten ml of human whole blood was drawn into a heparinized tube. The blood was lysed by the addition at room temperature of 90 ml of lysis buffer. The lysis buffer was 1% SDS in 1X Dulbecco phosphate buffered saline consisting of 138 mM NaCl, 8.1 mM $Na_2HPO_4$, 0.5 mM $MgCl_2$, 1.1 mM $KH_2PO_4$, and 2.7 mM KCl. At various times post-lysis, 5 ml aliquots of the lysed blood volume were vacumn filtered through either a 0.45 micron cellulose acetate membrane filter, 2.5 cm diameter, MSI, Inc., or a 0.45 micron nitrocellulose membrane filter, 2.5 cm diameter, Whatman Filters, (New Jersey). The membranes were then washed and treated as in Example 3, above, except that elution time was two hours at 42° C.

Results and Conclusions

As shown in Table 1, both nitrocellulose and cellulose acetate filters specifically and reversibly trapped high molecular weight DNA from lysed cells. However, cellulose acetate filters, on average performed better than nitrocellulose filters as measured by yield and purity of recovered DNA.

TABLE 1

|  | 2.5 CM Filter | Time (min) | OD260/ OD280 | μG Recovered from 0.5 mL |
|---|---|---|---|---|
| 1. | CELLULOSE ACETATE | 2 | 1.88 | 12.9 |
| 2. | CELLULOSE ACETATE | 10 | 1.76 | 14.0 |
| 3. | CELLULOSE ACETATE | 20 | 1.87 | 21.8 |
| 4. | CELLULOSE ACETATE | 30 | 1.79 | 12.5 |
| 5. | CELLULOSE ACETATE | 40 | 1.81 | 17.6 |
| 6. | CELLULOSE ACETATE | 50 | 1.79 | 15.8 |
| 7. | CELLULOSE NITRATE | 2 | 1.76 | 11.3 |
| 8. | CELLULOSE NITRATE | 10 | 1.73 | 17.2 |
| 9. | CELLULOSE NITRATE | 20 | 1.21 | IND* |
| 10. | CELLULOSE NITRATE | 30 | 1.35 | 8.15 |
| 11. | CELLULOSE NITRATE | 40 | 1.63 | 11.0 |
| 12. | CELLULOSE NITRATE | 50 | 1.64 | 10.8 |

*INDETERMINATE

The purity of DNA obtained by this method can be established by the ratio of absorbance at 260 nm to the absorbance at 280 nm. For highly purified DNA, this ratio is about 1.8 (Ausubel, F. M., et al., eds., *Current Protocols in Molecular Biology*, p. 2.2.3, John Wiley & Sons, New York, 1987). A limitation of the Millipore Filtration apparatus used in this experiment was a tendency for the lysate to leak around the O-ring gaskets in the filter holder. This resulted in a minor amount of residual lysate on the edge of the filters when they were removed prior to elution of the trapped DNA. Subsequently, this material contaminated the DNA recovered by elution. When the experiment was being analyzed by gel electrophoresis, this contamination source was inconsequential. When the DNA was subjected to spectral analysis, this contamination affected the measurements. When this problem was addressed by coating the O-rings with silicon grease prior to use, results, such as those presented in Table 1, were obtained. These results confirmed that the method of the invention generated highly purified DNA.

The time from lysis until movement of the lysate was through the filter device was varied from two minutes to 50 minutes. The time did not appear to affect the recovery of DNA, as shown in Table 1. It was observed that the time from lysis to filtration did not affect the time required to move the lysate through the filter, which in every case was less than one minute.

EXAMPLE 5

Rapid Recovery of DNA from Membrane Filters by Use of Microwave Radiation

The purpose of this example was to observe the effects of microwave radiation on the release of DNA trapped on the filter. Twelve Nucleopore ™ 0.45 micron cellulose acetate/nitrate membranes, 2.5 cm in diameter, Nucleopore Corp., Pleasanton, Calif. 94566, were used to extract DNA from human blood lysates as described in Example 3.

After filtration and washing, the filters were placed in 1.7 ml Eppendorf type tubes with screw-on caps and rubber O-rings. 1 ml of the elution buffer (described in Example 3) was added to each.

The elution was performed by exposing the tubes to one minute of microwave radiation in a Kenmore Model No. 565 8738310 Microwave oven in the defrost setting. This was sufficient to heat the tubes to about 60° C. The tubes were subjected to a second minute in the microwave after a brief exposure to cool water. Ultraviolet absorbance measurements were made on the liquid remaining in the tubes and are shown in Table 2.

TABLE 2

|   | 260 nM × 1000 | 280 nM × 1000 |
|---|---|---|
| 1. | 249 | 207 |
| 2. | 324 | 258 |

TABLE 2-continued

|   | 260 nM × 1000 | 280 nM × 1000 |
|---|---|---|
| 3. | 175 | 140 |
| 4. | 232 | 189 |
| 5. | 204 | 157 |
| 6. | 149 | 110 |
| 7. | 150 | 121 |
| 8. | 197 | 155 |
| 9. | 255 | 206 |
| 10. | 307 | 263 |
| 11. | lost tube | |
| 12. | 220 | 171 |

The average absorbance value of 0.219 at obtained at 260 nm corresponds to a recovery of DNA of about 64% based on normal blood values of 36 micrograms of DNA/ml of blood. The results in this Example indicate that a 1-minute exposure to microwave radiation can replace the more lengthy 2-hour procedure of Example 3. Use of the conditions of this Example significantly shorten the working time required to obtain substantially purified DNA using the method of the present invention.

EXAMPLE 6

Elution from Cellulose Acetate Filters with Various Solutions

The purpose of this example was to determine the effects of various cationic solutions on the release of DNA trapped on filter by the method of the present invention. Filter membranes retaining trapped DNA were prepared as in Example 3. The filters were removed from the apparatus and each placed in a shallow well of a Costar ™ plastic cell culture dish, and treated with one milliliter of elution buffer as described in Table 3. Elution was performed at 42° C. with gentle rocking on a thermostated rotary shaker for 15 minutes at which point the liquid was decanted and analyzed at 260 nM and 280 nM for the appearance of DNA.

The elution was continued by returning the liquid to the wells containing the filters and rocking for another six hours at 42° C. As in Example 3, the contents of the wells evaporated to dryness during this time. A milliliter of water was restored to each well and the dishes were placed back onto the shaker for 30 minutes just prior to analysis of the eluate. The results are presented in Table 3. Percent recovery, as shown in the right-hand column of Table 3, was based on the assumption of the presence of 5 million nucleated cells per milliliter of blood (36 micrograms DNA/ml) and 50 micrograms of DNA per OD260 unit.

TABLE 3

|  | 15 Min. 42° C. Elution | | 6 Hours 42° C. Elution | | | |
|---|---|---|---|---|---|---|
| Treatment Recovery | OD260 nM | OD280 nM | OD260 nM | OD280 nM | OD260/OD280 | % |
| 1. Water | .058 | .041 | .069 | .101 | 0.683 | 19 |
| 2. 80 nM Tris 20 NM (NH4)2(SO4) pH9 | .125 | .095 | .181 | .147 | 1.79 | 50 |
| 3. 2 + 1 nM MgCl2 | .068 | .046 | .191 | .145 | 1.32 | 53 |
| 4. 2 + 5 mM MgCl2 | .074 | .049 | .174 | .126 | 1.38 | 48 |
| 5. 2 + 10 mM MgCl2 | .169 | .120 | .282 | .204 | 1.38 | 78 |
| 6. 2 + 100 mM MgCl2 | .042 | .027 | .080 | .067 | 1.19 | 22 |
| 7. 2 + 10 mM ZnCl2 | No data | 50 1 precipitated | .098 | .088 | 1.11 | 27 |
| 8. 2 + 5% EtOH | .121 | .084 | .255 | .198 | 1.28 | 70 |
| 9. 2 + 10 mM CaCl2 | .057 | .034 | .108 | .101 | 1.06 | 30 |
| 10. 2 | .115 | .103 | .059 | .097 | 0.61 | 16 |
| 11. 2 + 10% EtOH | .074 | .052 | .111 | .083 | 1.33 | 30 |

TABLE 3-continued

| | 15 Min. 42° C. Elution | | 6 Hours 42° C. Elution | | | |
|---|---|---|---|---|---|---|
| Treatment Recovery | OD260 nM | OD280 nM | OD260 nM | OD280 nM | OD260/OD280 | % |
| 12. 2 + 100 Mm CaCl₂ | .062 | .041 | .121 | .092 | 1.31 | 33 |

These results indicated that of the 12 solutions tested, the solution containing 10 mM magnesium was preferred for the purpose of releasing and recovering the highest amount of DNA in a substantially purified form.

EXAMPLE 7

Effect of Restriction Enzyme

The purpose of this example was to determine the effects of restriction enzyme, heat, and microwave radiation on the release of DNA from the filter using the method of the present invention. Nucleopore TM filter membranes retaining trapped DNA were prepared as in Example 5. The filters with the trapped DNA were placed in Eppendorf tubes. To each tube was added 1 ml of elution buffer. The buffer, pH 9.0, was 20 mM in ammonium sulfate, 80 mM in Tris-HCl, and 10 mM in magnesium chloride. The tubes were subjected to several elution protocols as described below, and the eluted DNA was detected by its optical absorbance. TaqI, a restriction endonuclease, was obtained from New England Biolabs, Beverly, Mass. The microwave radiation was generated at "defrost" setting by a Kenmore Microwave Oven, model no. 56587383310 obtained from Sears, Los Angeles, Calif.

| Tubes | Protocol |
|---|---|
| 1,2 | Left at 60° C. with no additions for either 45 minutes or 90 minutes. |
| 3,4 | Left at 23° C. with no additions for either 45 minutes or 90 minutes |
| 5,6 | Left at 60° C. with addition of 50 Units of TaqI for either 45 minutes or 90 minutes |
| 7,8 | Microwaved at low power for 1 minute, measured, then allowed to sit for 45 minutes, then microwaved at low power for 1 minute. |

The results are shown in Table 4.

TABLE 4

| | 45 min | | 90 min | | | |
|---|---|---|---|---|---|---|
| | OD260 × 1000 | OD280 × 1000 | OD260 × 1000 | OD280 × 1000 | | |
| 1. | 141 | 097 | 162 | 106 | Microwaved | |
| 2. | 158 | 118 | 183 | 133 | 1 minute | |
| 3. | 053 | 041 | 117 | 082 | 213 | 152 |
| 4. | 103 | 094 | 193 | 161 | 258 | 202 |
| 5. | 168 | 130 | 213 | 158 | | |
| 6. | 226 | 179 | 272 | 218 | | |
| | Microwaved | | Microwaved | | | |
| | 1 minute | | 1 minute | | | |
| 7. | 453 | 366 | 460 | 368 | | |
| 8. | 251 | 198 | 285 | 222 | | |

The optical absorbance at 260 nm and 280 nm due to the quantity of TaqI used in this experiment was negligible. The results indicated that the concentration of restriction endonuclease used in this Example released some DNA trapped on the filter. However, the release of DNA was not as rapid as the release due to microwave radiation.

The results indicated that the fastest and most efficient release and recovery of DNA from these filters was accomplished by exposing to microwave radiation the filters retaining the trapped DNA in the presence of elution buffer containing magnesium.

Although the present invention has been described in considerable detail with regard to certain preferred versions, other versions are possible. For example, release of DNA trapped on the filter can be achieved by various treatments that are capable of cleaving long DNA chains. Such treatments might include freezing and thawing the filter retaining trapped DNA in eluting buffer. The filter with trapped DNA can be subjected to high temperatures achieved by any means. Any number of DNA-cleaving enzymes, including known restriction enzymes, can be used in the method of the present invention to release DNA trapped on the filter. Another mechanism for releasing the DNA trapped on the filter involves dissolving the filter device in an effective amount of a solvent, for example acetone. Alternatively, the DNA trapped on the filter can be released by application of an electric field, such as in electroelution of DNA molecules from agarose gels.

Other specific uses for the method of the present invention include combining the method of the present invention with polymerase chain reaction amplification of DNA sequences trapped, recovered or otherwise purified by the present method. DNA trapped and purified on the filter of the present invention can lend itself to other analytical procedures, including microscopic analysis by conventional or scanning probe microscopes. Various devices containing porous filters known in the art may be used.

It should be understood that any biological sample containing DNA in high molecular weight form is subject to the method of the present invention. The method of the present invention is applicable to the isolation and purification of DNA from any biological sample wherein the non-DNA components of the sample can be rendered to sufficiently small molecular aggregates so as to pass unobstructed through a porous filter capable of trapping the high molecular weight DNA. Such samples include stools, sputum, sperm and the like.

Furthermore, the method of the present invention can be used to separate genomic from non-genomic nucleic acid sequences, including RNA sequences.

The method of the present invention can be adapted for large scale DNA purification from large volumes of lysate from blood, other cells, and tissues. For example, such scale up can be achieved by employing larger filters.

It is apparent that many modifications and variations of this invention as set foth above may be made without departing from the spirit and scope. The specific embodiments described are given by way of example only, and the invention is limited only by the terms of the appended claims.

What is claimed is:

1. A method for rapidly obtaining substantially pure DNA from blood cells comprising the steps of:
   (a) avoiding high shear forces by gently lysing the membranes of said cells with a detergent to release the contents of the cells as a lysate containing high molecular weight DNA wherein said high molecular weight DNA comprises more than about 500,000 nucleotide base pairs per fragment;
   (b) allowing said lysate to stand from about two to about fifty minutes;
   (c) filtering said lysate through a membrane filter to selectively trap said high molecular weight DNA on the filter, wherein said filter comprises a porous substrate having a surface that reversibly and specifically traps said high molecular weight DNA, wherein said filter has a pore size from about 0.2 microns to about 0.8 microns
   (d) releasing said high molecular weight DNA from said filter using an aqueous solution comprising divalent cations selected from the group consisting of magnesium and calcium, wherein the cation concentration is less than about 100 mM; and
   (e) recovering said DNA in a substantially purified from said solution.

2. The method of claim 1 wherein said lysate is allowed to stand from about 5 to about 10 minutes.

3. The method of claim 1 wherein the step of lysing is performed at a temperature from about 0° C. to about 50° C.

4. The method of claim 1 wherein the sample is a tissue.

5. The method of claim 1 wherein the filter is comprised of a material selected from at least one of the group consisting of cellulose acetate, nitrocellulose, polyvinylidene and polycarbonate.

6. The method of claim 1 wherein the sample is whole blood.

7. The method of claim 1 wherein the filter comprises cellulose acetate and nitrocellulose having a pore size of 0.45 microns.

8. The method of claim 1 wherein the sample is a culture of cells.

9. The method of claim 1 wherein the detergent is sodium dodecyl sulfate.

10. The method of claim 1 wherein the lysate is filtered through said filter at a rate of from about 0.025 $ml/cm^2$/minute to about 0.5 $ml/cm^2$/minute.

11. The method of claim 10 wherein the rate is about 0.25 $ml/cm^2$/minute.

12. The method of claim 1 wherein said lysate is filtered through said filter by suction filtration.

13. The method of claim 1 wherein said lysate is filtered through said filter by centrifugation.

14. The method of claim 1 wherein the aqueous solution for releasing the high molecular weight DNA from said filter comprises substantially pure water.

15. The method of claim 1 wherein the aqueous solution comprises divalent cations.

16. The method of claim 15 wherein the divalent cations are selected from the group consisting of magnesium and calcium.

17. The method of claim 16 wherein the cation concentration is from about 1 mM to about 100 mM.

18. The method of claim 1 wherein said cation concentration is about 10 mM.

19. The method of claim 1 wherein the aqueous solution comprises a sufficient amount of restriction enzyme to release the DNA retained in the filter device.

20. The method of claim 1 wherein the step of releasing is performed at a temperature from about 0° to about 60° C.

21. The method of claim 1 wherein the step of releasing further comprises heating said filter.

22. The method of claim 21 wherein the filter is heated in an aqueous solution.

23. The method of claim 22 wherein the step of heating comprises contacting the filter in an aqueous solution with microwave radiation.

24. The method of claim 1 wherein the cells are rendered more susceptible to detergent lysis of their membranes.

25. The method of claim 24 wherein the cells are treated with a proteinase.

26. The method of claim 8 wherein the cells are mammalian.

27. The method of claim 8 wherein the cells are bacterial cells.

28. The method of claim 8 wherein the cells are yeast cells.

29. The method of claim 8 wherein the cells are plant cells.

* * * * *